United States Patent [19]

Aldrich et al.

[11] 4,251,659
[45] Feb. 17, 1981

[54] POLYFLUOROHYDROXYISOPROPYL-HETEROCYCLIC COMPOUNDS

[75] Inventors: Paul E. Aldrich, Wilmington, Del.; Gilbert H. Berezin, West Chester, Pa.

[73] Assignee: E. I. Du Pont de Nemours and Company, Wilmington, Del.

[21] Appl. No.: 863,266

[22] Filed: Dec. 22, 1977

Related U.S. Application Data

[63] Continuation-in-part of Ser. No. 793,712, May 6, 1977, abandoned, which is a continuation-in-part of Ser. No. 699,588, Jun. 24, 1976, abandoned.

[51] Int. Cl.$^3$ .................. C07D 209/08; C07D 215/04; C07D 223/16
[52] U.S. Cl. ........................... 546/102; 260/239 BB; 260/326.11 R; 546/108; 546/166
[58] Field of Search ......... 260/319.1, 326.11, 239 BB; 261/289 H, 289 C; 546/166, 102, 108

[56] References Cited

U.S. PATENT DOCUMENTS 4,058,612  11/1977  Neustadt ............................. 429/251

FOREIGN PATENT DOCUMENTS 1394373  5/1975  United Kingdom .
1394374  5/1975  United Kingdom .

*Primary Examiner*—Jose Tovar
*Assistant Examiner*—D. B. Springer

[57] ABSTRACT

Polyfluorohydroxyisopropyl: -indolines, -tetrahydroquinolines, and -benzazepines, such a α,α-bis(trifluoromethyl)-1,2,3,4-tetrahydroquinoline-6-methanol, useful as intermediates for antihypertensives.

5 Claims, No Drawings

POLYFLUOROHYDROXYISOPROPYL-HETEROCYCLIC COMPOUNDS

RELATED APPLICATION

This application is a continuation-in-part of copending application Ser. No. 793,712, filed May 6, 1977, now abandoned which in turn is a continuation-in-part of application Ser. No. 699,588, filed June 24, 1976, now abandoned.

BACKGROUND

This invention relates to polyfluorohydroxyisopropyl-heterocyclic compounds.

Sheppard, W. A., *J. Am. Chem. Soc.*, 87 (11), 2410 (1965) and Gilbert, E. E. et al., *J. Org. Chem.*, 30, 1001 (1965) disclose a process for adding hexafluoroacetone to aniline derivatives to give α,α-bis(trifluoromethyl)-p-aminobenzyl alcohols.

Jones, E. S., in U.S. Pat. No. 3,405,177 discloses the use of sulfonic acid catalysis in this reaction.

German OS No. 2,552,993 discloses compounds containing a ureido or isoureido function which have utility as antihypertensive agents.

The compounds of this invention are useful as intermediates in the preparation of antihypertensive compounds, which are claimed in applicant's concurrently filed application Ser. No. 863,270, filed Dec. 22, 1979, 1977, which is a continuation-in-part of Ser. No. 793,711, filed May 6, 1977, which, in turn, is a continuation-in-part of Ser. No. 699,587, filed June 24, 1976.

SUMMARY

According to this invention there is provided compounds of the following formula and processes for preparing them.

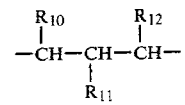

where $R_1 + R_2$, taken together, can be:

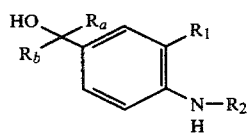  (a)

where
$R_6 =$ H or —CH$_3$;
$R_7 =$ H or —CH$_3$;
$R_8 =$ H or alkyl of 1-4 carbons;
$R_9 =$ H or alkyl of 1-4 carbons; or
$R_8 + R_9$, taken together, can be —(CH$_2$)$_4$—;
provided
(i) at least one of $R_6$, $R_7$, $R_8$, or $R_9$ = H; and
(ii) the sum of the carbons of $R_6$, $R_7$, $R_8$ and $R_9$ is not more than 6;

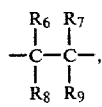  (b)

where
$R_{10} =$ H, —CH$_3$, or —CH$_2$CH$_3$;
$R_{11} =$ H, —CH$_3$, or —CH$_2$CH$_3$;
$R_{12} =$ H, —CH$_3$, or —CH$_2$CH$_3$; or
$R_{11}$, taken together with $R_{10}$ or $R_{12}$, can be —(CH$_2$)$_4$—;

provided at least one of $R_{10}$, $R_{11}$, or $R_{12}$ = H; or (c) —(CH$_2$)$_4$—;

$R_a$ is CF$_3$, CF$_2$Cl, or CF$_2$H; and
$R_b$ is CF$_3$, CF$_2$Cl, or CF$_2$H.

PREFERRED COMPOUNDS

Preferred compounds for preparing antihypertensive compounds with a high degree of activity are those compounds where $R_1$ and $R_2$, taken together, are

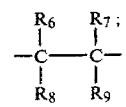

and $R_6$, $R_7$, and $R_8$ are hydrogen.

Also preferred are those compounds where $R_1$ and $R_2$, taken together, are

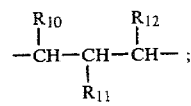

and $R_{10}$ and $R_{11}$ are hydrogen.

Also preferred are those compounds where $R_a$ is CF$_3$ and $R_b$ is CF$_3$, CF$_2$Cl or CF$_2$H.

DETAILED DESCRIPTION

Compounds where $R_a$ and $R_b$ both are CF$_3$ are prepared according to the following general reaction:

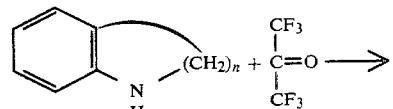

n = 2 to 4

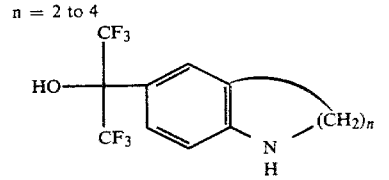

The reaction is conducted in a sealed pressure reactor at temperatures from 80°-200° C.; it can also be conducted in a refluxing solvent, such as benzene or toluene, in a flask with hexafluoroacetone sesquihydrate or trihydrate. Acidic catalysts such as AlCl$_3$, BF$_3$, or p-toluenesulfonic acid can be used but are not necessary.

Reaction time is usually 4–12 hours. A temperature of 100°–120° C. and use of 1–5 mole percent of AlCl₃ are preferred.

A modified method for preparing these compounds, and all compounds where $R_a$ and $R_b$ are as defined, which produces higher yields for many of the compounds, especially the indolines, involves attaching a suitable protective group, such as benzyl or substituted benzyl, at the basic nitrogen atom of the amine starting material, then contacting this protected compound with hexafluoroacetone, pentafluoroacetone, chloropentafluoroacetone, or 1,1,3,3-tetrafluoroacetone. The following diagram shows, in a general way, this reaction scheme illustrated by initial reaction of a benzyl halide followed by reaction of a protected compound with hexafluoroacetone:

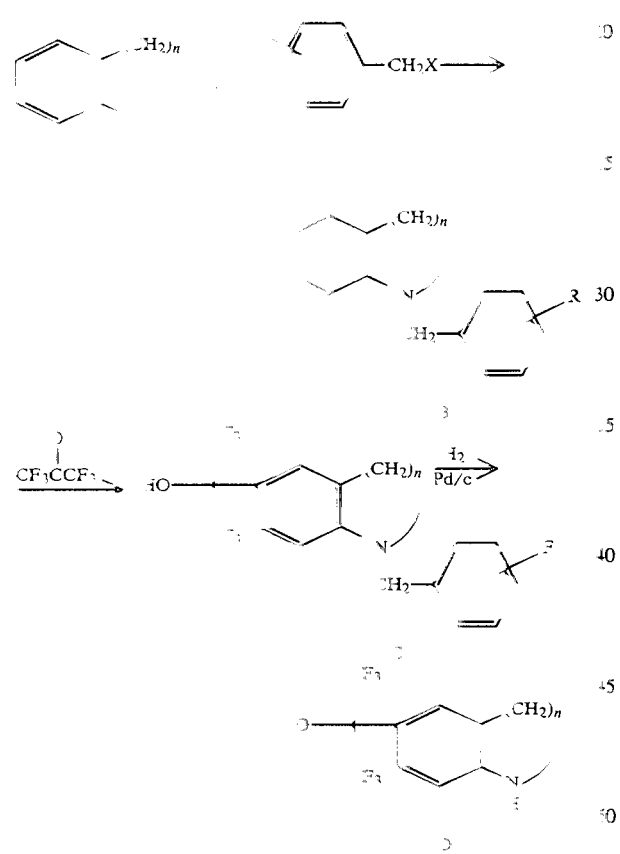

where
X = Cl or Br;
R = H, F, Cl, Br, NO₂, phenyl, or CH₃;
n = 2, 3, or 4.

Starting amine (A) is treated with a benzyl halide to give a tertiary N-benzylamine (B). This is heated with hexafluoroacetone (or pentafluoroacetone or chloropentafluoroacetone) to give the adduct C, which is then hydrogenated to remove the benzyl group to give the desired compound (D). The addition of the less reactive 1,1,3,3-tetrafluoroacetone to N-benzylamine (B) is advantageously catalyzed by anhydrous aluminum chloride.

In a similar reaction procedure, the benzyl halide can be replaced by benzhydryl chloride or bromide in formation of a protected compound. The protected compound (including adduct (B) above) can be treated with either hexafluoroacetone, pentafluoroacetone, chloropentafluoroacetone, 1,3-dichlorotetrafluoroacetone, or 1-chloro-1,1,3,3-tetrafluoroacetone followed by hydrogenation.

Thus, the latter portion of this process comprises contacting hexafluoroacetone, pentafluoroacetone, chloropentafluoroacetone, 1,1,3,3-tetrafluoroacetone, 1,3-dichlorotetrafluoroacetone, or 1-chloro-1,1,3,3-tetrafluoroacetone with

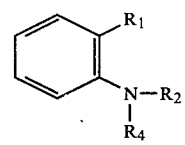

where $R_1$ and $R_2$ are as defined and $R_4$ is H, $(C_6H_5)_2CH$, or

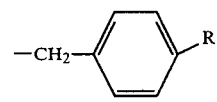

where R = H, F, Cl, Br, NO₂, phenyl or CH₃; followed by a step of hydrogenolysis.

The hydrogenation step occasionally requires excess acid as a co-catalyst. Hydrogenolysis is attempted without addition of acid, and if little or no uptake of hydrogen is observed, acid is added (for example, concentrated hydrochloric acid), and the reaction is allowed to proceed.

The amine starting materials are either known in the art or easily prepared from those known in the art. Methods for making the various ring systems, however, are outlined as follows:

Indolines

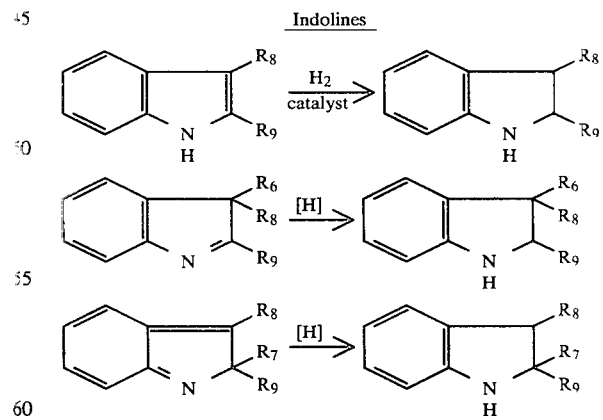

Tin and hydrochloric acid or zinc and hydrochloric acid can also be used as reducing agents.

See Elderfield, R. C., *Heterocyclic Compounds*, Vol. 3, John Wiley & Sons, Inc., New York, N.Y. (1952), p.1.

Tetrahydroquinolines

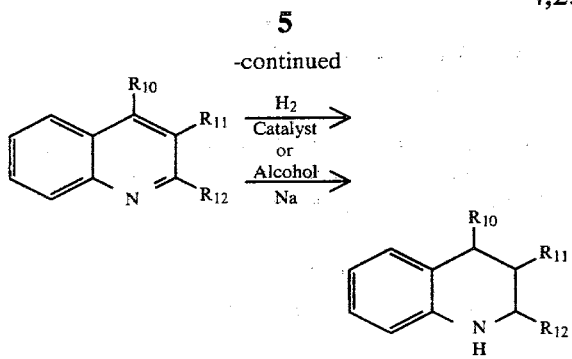

See Elderfield, R. C., *Heterocyclic Compounds* Vol. 4, John Wiley & Sons, Inc. New York, N.Y. (1952) p.1.

Benzazepines

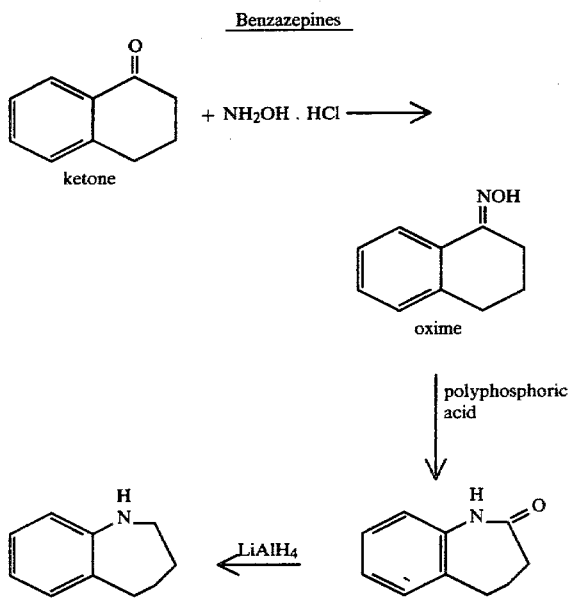

In the reaction scheme outlined 3,4-dihydro-1(2H)-naphthalenone is contacted with hydroxylamine hydrochloride to give the corresponding oxime.

The oxime is rearranged by treatment with polyphosphoric acid to give the lactam 1,3,4,5-tetrahydro-1H-1-benzazepin-2-one.

Reduction of the lactam with LiAlH$_4$ gives 2,3,4,5-tetrahydro-1H-1-benzazepine.

The following examples further illustrate the methods for synthesis of these compounds. All parts are by weight and all temperatures are in degrees centigrade unless otherwise indicated.

EXAMPLE 1

α,α-bis(Trifluoromethyl)-1,2,3,4-tetrahydro-6-quinolinemethanol

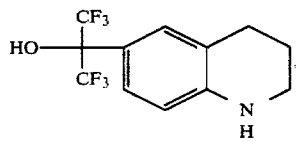

Two hundred grams of 1,2,3,4-tetrahydroquinoline and 2 g anhydrous aluminum chloride are added to a one liter stainless steel reactor. The reactor is cooled and evacuated, 265 g (1.60 moles) hexafluoroacetone is added, and it is sealed and heated to 120° C. with shaking for ten hours. The reactor is then cooled to room temperature and vented. The contents are decanted to give a red semicrystalline solid, which is treated with 250 ml of methylene chloride and filtered. The filter cake is washed with three additional 250 ml portions of methylene chloride. The residual orange solid is treated with decolorizing carbon in hot chlorobutane and filtered. From the filtrate is obtained 310 g (1.04 moles) α,α-bis(trifluoromethyl)-1,2,3,4-tetrahydro-6-quinolinemethanol, as a pale yellow crystalline solid, m.p. 115°–116° C.

Anal. Calcd. for $C_{12}H_{11}F_6NO$: C, 48.17; H, 3.71; N, 4.68. Found: C, 48.46; H, 4.06; N, 4.93.

EXAMPLE 2

α,α-Bis(trifluoromethyl)-2,3-dihydro-1H-indole-5-methanol

A. 1-Benzylindoline

To a stirred refluxing mixture of 119 g (1 mole) of indoline, 800 ml of toluene (other solvents, e.g. isopropyl alcohol, are satisfactory), and 207 g (1.5 mole) of pulverized, anhydrous potassium carbonate is added dropwise 126.5 g (1 mole) of benzyl chloride. When addition is complete, refluxing is continued until evolution of gas ceases as evidenced by a gas meter (about three hours). The mixture is allowed to cool, and the solids are removed by filtration. The filtrate is evaporated, and the residue is distilled to give 153 g (73%) of 1-benzylindoline, b.p. 162°–165° (4.5 mm).

B.

1-Benzyl-α,α-bis(trifluoromethyl)-2,3-dihydro-1H-indole-5-methanol

A stirred mixture of 83.6 g (0.4 mole) of 1-benzylindoline, 250 ml of toluene, and 77.2 g (0.4 mole) of hexafluoroacetone sesquihydrate is refluxed for four hours. The mixture is then refluxed under Dean-Stark conditions until all water is removed. The solution is evaporated. The residue is dissolved in 500 ml of methylcyclohexane (heating, if necessary) and allowed to crystallize under nitrogen atmosphere. The gummy crystals are filtered off, washed, and dried to give 116.3 g (77%) of 1-benzyl-α,α-bis(trifluoromethyl)-2,3-dihydro-1H-indole-5-methanol, m.p. 85°–90°. Because solutions of these crystals oxidize readily, further purification by recrystallization entails needless loss; therefore, the crude crytals are used for the next step.

C.

α,α-Bis(trifluoromethyl)-2,3-dihydro-1H-indole-5-methanol

A mixture of 55 g (0.15 mole) of 1-benzyl-α,α-bis(trifluoromethyl)-2,3-dihydro-1H-indole-5-methanol, 200 ml of alcohol, 32 ml of concentrated hydrochloric acid, and 2 g of 10% palladium on charcoal is shaken in a Parr apparatus at an initial pressure of three atmospheres until no further change of pressure is observed. The catalyst is filtered off, and the filtrate is evaporated. The residue is distributed between ether and 8 N ammonium hydroxide. The ether layer is separated, washed (saturated sodium chloride solution), dried (magnesium sulfate), and evaporated. Dibutyl ether is added to the residue, and the solution is cooled in an ice bath. The crystals are filtered off to give 33.3 g (80%) of α,α-bis(trifluoromethyl)-2,3-dihydro-1H-indole-5-methanol, m.p. 161°-162°.

EXAMPLE 3

Example 2 is followed except p-nitrobenzyl chloride is used in place of benzyl chloride. The first intermediate, 1-p-nitrobenzylindoline, m.p. 95°-97° is obtained. This is then converted to the second intermediate, 1-p-nitrobenzyl-α,α-bis(trifluoromethyl)-2,3-dihydro-1H-indole-5-methanol. This is inconvenient to purify because of reaction of its solutions with air, so it is promptly hydrogenated to give α,α-bis(trifluoromethyl)-2,3-dihydro-1H-indole-5-methanol, m.p. 160°-161°.

EXAMPLES 4-17

Using the procedure of Examples 1 or 2, the following compounds can be made from the appropriate starting material which is shown.

| Starting Material | Product |
|---|---|
| indoline | 5-[C(OH)(CF₃)₂]-indoline, m.p. 159°-160° |
| 3-methylindoline | 5-[C(OH)(CF₃)₂]-3-methylindoline, m.p. 163°-164° |
| 4-methyl-1,2,3,4-tetrahydroquinoline | 6-[C(OH)(CF₃)₂]-4-methyl-1,2,3,4-tetrahydroquinoline, m.p. 158°-159° |
| 3-methyl-1,2,3,4-tetrahydroquinoline | 6-[C(OH)(CF₃)₂]-3-methyl-1,2,3,4-tetrahydroquinoline |
| 2-methyl-1,2,3,4-tetrahydroquinoline | 6-[C(OH)(CF₃)₂]-2-methyl-1,2,3,4-tetrahydroquinoline, m.p. 93°-94° |
| 4-ethyl-1,2,3,4-tetrahydroquinoline | 6-[C(OH)(CF₃)₂]-4-ethyl-1,2,3,4-tetrahydroquinoline |
| 3-ethyl-1,2,3,4-tetrahydroquinoline | 6-[C(OH)(CF₃)₂]-3-ethyl-1,2,3,4-tetrahydroquinoline |

EXAMPLE 18

α-(Chlorodifluoromethyl)-α-(trifluoromethyl)-2,3-dihydro-1H-indole-5-methanol

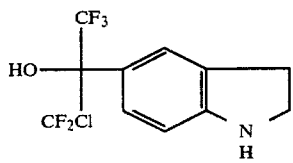

A.
1-Benzyl-α-(chlorodifluoromethyl)-α-(trifluoromethyl)-2,3-dihydro-1H-5-methanol A mixture of 41.8 g (0.2 mole) of 1-benzylindoline, 300 ml of toluene, 8 ml of water, and 40.2 g (0.22 mole) of chloropentafluoroacetone is refluxed for 16 hours. The mixture is then refluxed under Dean-Stark conditions until all water is removed. The toluene is removed by evaporation to give 70 g of residue, which is crude benzyl-α-(chlorodifluoromethyl)-α-(trifluoromethyl)-2,3-dihydro-1H-5-methanol. The crude material is used to obtain the desired product, as described in part B.

α-(Chlorodifluoromethyl)-α-(trifluoromethyl)-2,3-dihydro-1H-indole-5-methanol

The crude material from part A is dissolved in a mixture of 150 ml of alcohol and 20 ml of concentrated hydrochloric acid. The solution is hydrogenated in the presence of 2 g of 10% palladium on carbon in a Parr shaker apparatus at an initial pressure of three atmospheres until the gauge indicates that uptake of hydrogen is complete. The catalyst is filtered off, and the filtrate is evaporated. The residue is dissolved in water, made alkaline with concentrated NH₄OH and extracted with ether. The ether solution is dried and evaporated. The residue is recrystallized from methylcyclohexane to give 29.6 g (49%) of α-chlorodifluoromethyl)-α-(trifluoromethyl)-2,3-dihydro-1H-indole-5-methanol, m.p. 140°–143°. The structure is confirmed by the nmr spectrum and elemental analysis.

Anal. Calcd. for $C_{11}H_9ClF_5NO$: C, 43.80; H, 3.01; N, 4.65. Found: C, 43.56; H, 3.02; N, 4.66.

EXAMPLE 19

α-(Difluoromethyl)-α-(trifluoromethyl)-2,3-dihydro-1H-indole-5-methanol

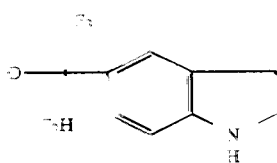

The procedure of Example 18, part A is followed except that (1) pentafluoroacetone is used in place of chloropentafluoroacetone and (2) after water removal the toluene solution is treated with anhydrous hydrogen chloride to precipitate the hydrochloride salt of 1-benzyl-α-(difluoromethyl)-α-(trifluoromethyl)-2,3-dihydro-1H-indole-5-methanol, m.p. 115°–118°.

The salt is then hydrogenated as in part B of Example 18. Recrystallization of the product from dibutyl ether gives α-(difluoromethyl)-α-(trifluoromethyl)-2,3-dihydro-1H-indole-5-methanol, m.p. 129°–132°. The structure is confirmed by nmr spectroscopy and by elemental analysis.

Anal. Calcd. for $C_{11}H_{10}F_5NO$: C, 49.44; H, 3.77; N, 5.24. Found: C, 49.29; H, 3.71; N, 5.48.

EXAMPLE 20

α,α-Bis(difluoromethyl)-2,3-dihydro-1H-indole-5-methanol

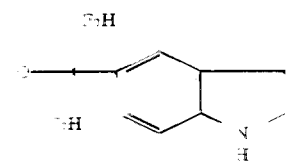

A mixture of 41.8 g (0.2 mole) of 1-benzylindoline, 150 ml of toluene, 1 g of anhyd aluminum chloride, and 26.0 g of sym-tetrafluoroacetone is heated in an acid-resistant bomb (e.g. Hastelloy ®) at 120° for 8 hours.

The solvent is removed by evaporation, and the residue is purified by chromatography on silica gel with elution by 60:10:30 toluene-ethyl acetate-hexane. Desired fractions containing 1-benzyl-α,α-bis-(difluoromethyl)-2,3-dihydro-1H-indole-5-methanol are identified by the nmr spectrum which shows a difluoromethyl proton centered at 6.08 ppm with a coupling constant with fluorine of 48 hz.

The combined desired fractions are hydrogenated in a mixture of 150 ml of alcohol and 20 ml of concentrated hydrochloric acid with 0.5 g of 10% palladium on carbon as catalyst in a Parr shaker apparatus at an initial pressure of 3 atmospheres. When the gauge indicates that uptake is complete, the catalyst is removed by filtration, and the filtrate is evaporated. The residue is dissolved in water, and an equal volume of saturated aqueous potassium carbonate is added. The mixture is extracted with ether. The ether solution is dried and evaporated. The residue is recrystallized from methylcyclohexane to give 8.4 g of α,α-bis(difluoromethyl)-2,3-dihydro-1H-indole-5-methanol, m.p. 130.5°–133.5°. The structure is confirmed by nmr spectroscopy and elemental analysis.

Anal. Calcd. for $C_{11}H_{11}F_4NO$: C, 53.01; H, 4.45. Found: C, 53.26; H, 4.49.

EXAMPLE 21

α,α-bis(Chlorodifluoromethyl)-2,3-dihydro-1H-indole-5-methanol

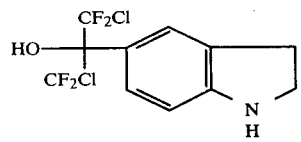

A. 1-Benzhydryl-indoline

A mixture of 49.4 g (0.2 mole) of bromodiphenylmethane (an equimolar quantity of chlorodiphenylmethane may be used instead), 23.8 g (0.2 mole) of indoline, 55.2 g (0.4 mole) of anhydrous potassium carbonate, and 200 ml of toluene is refluxed for 16 hrs under nitrogen with good stirring. The salts are removed by filtration, and the solvent is evaporated. The residue is chromatographed on silica gel with 30:70 toluene-hexane as the eluent. The product is a viscous oil, which can be crystallized from ethanol to give 1-benzhydryl-indoline, m.p. 62°–63.5°. The structure is confirmed by nmr spectroscopy and elemental analysis:

Anal. Calcd. for $C_{21}H_{19}N$: C, 88.38; H, 6.71; N, 4.91. Found: C, 88.03; H, 6.85; N, 4.96.

B.

α,α-bis(Chlorodifluoromethyl)-2,3-dihydro-1H-indole-5-methanol

A mixture of 14.5 g (0.05 mole) of 1-benzhydryl-indoline, 100 ml of toluene, 2 ml of water, and 10.9 g (0.055 mole) of 1,3-dichlorotetrafluoroacetone is refluxed for 3 hrs. Another 10.9 g portion of 1,3-dichlorotetrafluoroacetone is added, and refluxing is continued for 13 hrs. The moisture is then removed azeotropically, and the solvent is evaporated to give a crude, viscous residue of 1-benzhydryl-α,α-bis(chlorodifluoromethyl)-2,3-dihydro-1H-indole-5-methanol. This crude material is tedious to purify and is more conveniently used without further purification for conversion to the desired product.

The crude 1-benzhydryl-α,α-bis(chlorodifluoromethyl)-2,3-dihydro-1H-indole-5-methanol is dissolved in a mixture of 200 ml of alcohol and 20 ml of concentrated hydrochloric acid and is hydrogenated at an initial pressure of three atmospheres in the presence of 1.5 g of 10% palladium on charcoal in a Parr shaker apparatus until no further change of pressure is observed. The catalyst is filtered off, and the filtrate is evaporated. The residue is evaporated repeatedly with toluene to remove traces of water. Trituration of the residue with toluene gives crystals, which are filtered off to give 6.2 g of α,α-bis(chlorodifluoromethyl)-2,3-dihydro-1H-indole-5-methanol hydrochloride, m.p. 224°–228° (dec.). For analysis a portion is recrystallized from nitromethane to give crystals, m.p. 228°–229° (dec.). The structure is confirmed by nmr spectroscopy and elemental analysis:

Anal. Calcd. for $C_{11}H_9Cl_2F_4NO \cdot HCl$: C, 37.26; H, 2.84; N, 3.95. Found: C, 37.57; H, 2.79; N, 4.08.

The free base, α,α-bis(chlorodifluoromethyl)-2,3-dihydro-1H-indole-5-methanol, m.p. 109°–112°, is prepared by stirring the hydrochloride salt with aqueous ammonium hydroxide and extraction with ether. Evaporation of the ether extract and recrystallization of the residue from methylcyclohexane gives the free base.

EXAMPLE 22

α-(Chlorodifluoromethyl)-α-(difluoromethyl)-2,3-dihydro-1H-indole-5-methanol

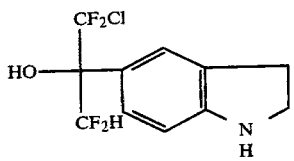

A mixture of 1.7 g of 1-benzhydryl-indole (Example 21, part A), 100 ml of dichloromethane, and 5 ml of 1-chloro-1,1,3,3-tetrafluoroacetone is refluxed under nitrogen for 6 hours. The solvent is evaporated to give a green residue of crude 1-benzhydryl-α-(chlorodifluoro)-α-(difluoromethyl)-2,3-dihydro-1H-indole-5-methanol. This intermediate is tedious to purify and is more conveniently converted to the desired product without further purification.

The crude 1-benzhydryl-α-(chlorodifluoro)-α-(difluoromethyl)-2,3-dihydro-1H-indole-5-methanol is hydrogenated in a mixture of 150 ml of alcohol and 20 ml of concentrated hydrochloric acid with 0.2 g of 10% palladium on charcoal as catalyst in a Parr shaker apparatus at an initial pressure of two atmospheres until a gauge indicates that uptake is complete (less than two hours). The catalyst is filtered off, and the filtrate is evaporated. The residue is dissolved in water containing a little 6 N HCl to ensure solution. Then excess concentrated ammonium hydroxide is added, and the oil that separates is extracted with ether. The ether extract is dried and evaporated. The residue is recrystallized from a 50:50 mixture of methylcyclohexane and dibutylether to give 0.9 g (54%) of α-(chlorodifluoro)-α-(difluoromethyl)-2,3-dihydro-1H-indole-5-methanol, m.p. 112.5°–115°. The structure is confirmed by nmr spectroscopy (CDCl₃), especially by observing the spectrum after exchange with deuterium oxide.

What is claimed is:

1. A compound of the formula

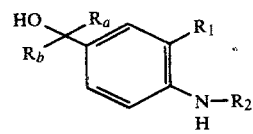

where $R_1 + R_2$, taken together, can be

where
$R_6 = H$ or $-CH_3$;
$R_7 = H$ or $-CH_3$;
$R_8 = H$ or alkyl of 1–4 carbons;
$R_9 = H$ or alkyl of 1–4 carbons; or
$R_8 + R_9$, taken together, can be $-(CH_2)_4-$;
provided
  (i) at least one of $R_6$, $R_7$, $R_8$, or $R_9 = H$; and
  (ii) the sum of the carbons of $R_6$, $R_7$, $R_8$, and $R_9$ is not more than 6;

$$\begin{array}{ccc} R_{10} & & R_{12} \\ | & & | \\ -CH-CH-CH- \\ & | & \\ & R_{11} & \end{array} \quad (b)$$

where
$R_{10} = H$, $-CH_3$, or $-CH_2CH_3$;
$R_{11} = H$, $-CH_3$, or $-CH_2CH_3$;
$R_{12} = H$, $-CH_3$, or $-CH_2CH_3$; or
$R_{11}$, taken together with $R_{10}$ or $R_{12}$ can be $-(CH_2)_4-$;
provided at least one of
$R_{10}$, $R_{11}$, or $R_{12} = H$; or (c) $-(CH_2)_4-$;
$R_a$ is $CF_3$, $CF_2Cl$, or $CF_2H$; and
$R_b$ is $CF_3$, $CF_2Cl$, or $CF_2H$.

2. A compound of claim 1 where $R_1$ and $R_2$, taken together, are

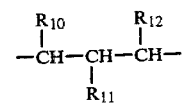

and $R_6$, $R_7$, and $R_8$ are hydrogen.

3. A compound of claim 1 where $R_1$ and $R_2$, taken together, are

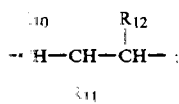
and $R_{10}$ and $R_{11}$ are hydrogen.
4. A compound of claim 1 where $R_a$ and $R_b$ both are $CF_3$.
5. A compound of claim 1 wherein $R_a$ is $CF_3$ and $R_b$ is $CF_3$, $CF_2Cl$ or $CF_2H$.
* * * * *